United States Patent
Reddy et al.

(10) Patent No.: US 10,328,173 B2
(45) Date of Patent: Jun. 25, 2019

(54) LONG-ACTING DEODORIZATION OF NOXIOUS ODORS USING A WATER-BASED DEODORIZING SOLUTION IN AN ULTRASONIC DISPENSER

(71) Applicant: APPTEC, Inc., Cranbury, NJ (US)

(72) Inventors: Vilambi N R K Reddy, Cranbury, NJ (US); Anil Torgalkar, Cranbury, NJ (US)

(73) Assignee: APPTEC, Inc., Cranbury, NJ (US)

( * ) Notice: Subject to any disclaimer, the term of this patent is extended or adjusted under 35 U.S.C. 154(b) by 0 days.

(21) Appl. No.: 16/154,340

(22) Filed: Oct. 8, 2018

(65) Prior Publication Data

US 2019/0038794 A1    Feb. 7, 2019

(51) Int. Cl.
| | |
|---|---|
| A61L 9/14 | (2006.01) |
| A61L 9/12 | (2006.01) |
| B05B 17/06 | (2006.01) |
| B05B 17/00 | (2006.01) |
| A61L 9/013 | (2006.01) |

(52) U.S. Cl.
CPC .............. *A61L 9/122* (2013.01); *A61L 9/14* (2013.01); *B05B 17/0646* (2013.01); *B05B 17/0653* (2013.01); *A61L 9/013* (2013.01); *A61L 2209/132* (2013.01)

(58) Field of Classification Search
CPC ........ A61L 9/14; A61L 9/122; B05B 17/0646
See application file for complete search history.

(56) References Cited

U.S. PATENT DOCUMENTS

| | | |
|---|---|---|
| 9,993,573 B1 | 6/2018 | Reddy et al. |
| 2005/0279854 A1 | 12/2005 | Martens, III et al. |
| 2006/0249144 A1* | 11/2006 | DeHaan ............ A61M 15/0085 |
| | | 128/200.14 |
| 2009/0071515 A1* | 3/2009 | Prokopenko .............. B08B 3/12 |
| | | 134/56 R |
| 2009/0159719 A1 | 6/2009 | Millet |
| 2015/0076716 A1 | 3/2015 | Roemburg et al. |

* cited by examiner

*Primary Examiner* — Sean E Conley
(74) *Attorney, Agent, or Firm* — Stanley H. Kremen

(57) ABSTRACT

A long-acting ultrasonic dispenser that effuses a water-based deodorizer solution into ambient air as a dry fog in a closed environment, and a method for deodorizing noxious odors in that closed environment by the dry fog. The dry fog, containing the deodorizer, chemically reacts with materials producing the odors, thereby neutralizing them. The dispenser contains an electronic ultrasonic wave generator comprising a piezoelectric crystal and an ultrasonic membrane, which is always submerged under liquid. As the liquid evaporates, droplets larger than five microns are filtered out, and the remaining dry fog is emitted into the air. The dispenser is connected to a large reservoir. When the liquid level reaches a minimum permissible height, additional deodorizer solution is pumped into the dispenser. This system is ideal for use with central air conditioners in large office buildings to eliminate odors over a long period of time with minimum maintenance.

17 Claims, 1 Drawing Sheet

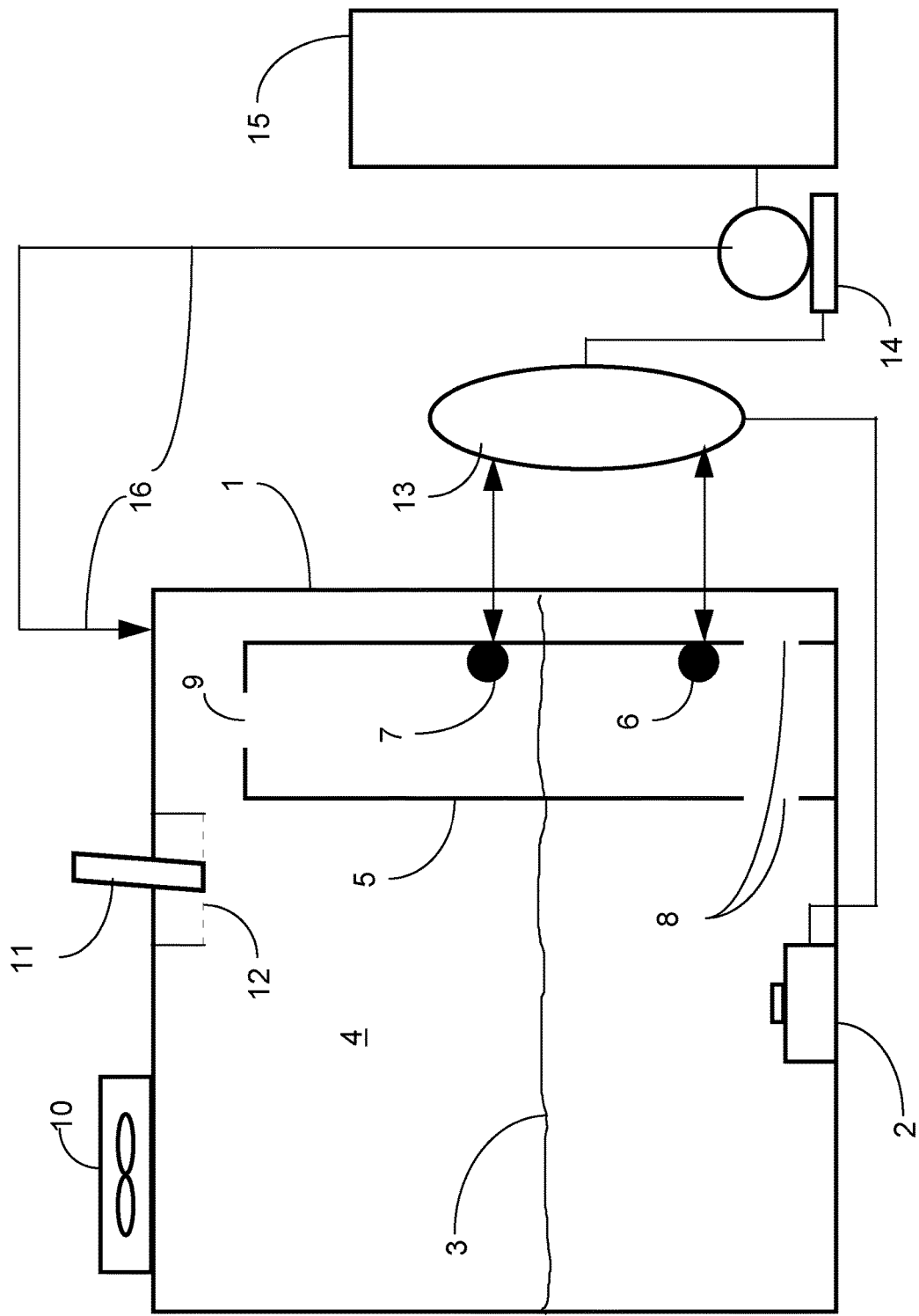

LONG-ACTING DEODORIZATION OF NOXIOUS ODORS USING A WATER-BASED DEODORIZING SOLUTION IN AN ULTRASONIC DISPENSER

CROSS REFERENCE TO RELATED APPLICATIONS

This Present application is related to our U.S. Pat. No. 9,993,573 issued on Jun. 12, 2018 for our invention entitled, "Odor Neutralizer." It is also related to U.S. patent application Ser. No. 15/400,964 filed on Jan. 2, 2016 for our invention entitled, "Programmable Dispenser." Both U.S. Pat. No. 9,993,573 and U.S. patent application Ser. No. 15/400,964 are incorporated by reference in their entirety herein.

BACKGROUND

The prior art comprises many devices to produce fine mists. The most common of these devices are spray cans that use a chemical propellant to impel a liquid substance through a nozzle. The liquid substance can be water based, alcohol based, or oil based. Less common are pump cans or bottles that utilize mechanical pressure to impel the liquid substance through the nozzle. Vaporizers are available that use heat to expand the liquid, thereby also using pressure to propel it through the nozzle. Finally, ultrasonic devices are used to produce the mist that is impelled through the nozzle.

Fine mist dispensers for oil-based substances must be disposable because the liquid will ultimately clog the nozzle after repeated use. Ultrasonic devices that are not disposable depend upon transport of the liquid substance to a vibrating membrane usually via a saturated wick. The wick can be fabricated from cotton, but other substrates have been used. These ultrasonic devices are best suited to produce an aqueous mist because alcohol evaporates too rapidly to maintain transport of the liquid from the reservoir to the membrane. To be effective, the saturated wick must be in constant contact with the membrane so that there is a liquid film that will be ultrasonically atomized. Thus, these ultrasonic devices are atomizers used principally to produce fine aqueous mists.

Ultrasonic mist dispensers are currently available. They require a small amount of electric current to induce vibration of the membrane at ultrasonic frequencies. A piezoelectric crystal may be used to produce the vibration. Most of these ultrasonic devices are small and portable. Ideally, the liquid to be atomized is distilled water to avoid clogging of the nozzle. Such a liquid substance is used in cool humidifiers. The water vapor thus fills a room, thereby raising the humidity. However, the liquid to be atomized may also contain other chemicals in aqueous solution. These chemicals may include incense, perfumes, airborne inhalation medications, odor neutralizers, and harmless insecticides. Unfortunately, constant production of mists including these chemical substances can be too intense. How often do people go into elevators and smell the annoying odor of lingering perfume. While incense can be useful for aromatherapy, the smell of too much incense can annoy rather than soothe. Too much inhalation medicine in the air could be detrimental to health.

Consumer desires to eliminate noxious odors has fueled a modern industry beginning in the twentieth century. Some bad odors can be eliminated merely by lighting a match or otherwise using fire. In the 1960's, Renuzit® marketed spray cans that filled the surrounding air with fragrances, such as baby powder, to mask odors. These were and are still marketed by that company as air fresheners. Today, Renuzit® sells "cones" containing fragrance gels and "pearls" that both absorb odors and emit pleasing fragrances. Air fresheners are marketed by Glade®, which also markets odor-eliminating candles. Rubbermaid® sells plug-in cartridges that continuously fill a room with a desired fragrance (e.g., citrus scent). Odorklenz® sells products that neutralize some odors such as those from urine. Duluth Trading Co. sells an "odor eliminator" that runs on four C-batteries and uses electrically charged "activated oxygen" in footwear and gloves. This device claims to eliminate odors arising from sweat, mold, mildew, germs, toxins, and pollutants. Hamilton Beach® sells an electronic True Air® Room Odor Eliminator that uses a fan to force room air through three carbon filters, which neutralize the odors, and optionally add fragrances to the air. Biocide Systems™ markets a product that uses chlorine dioxide (ClO2) to neutralize odors. This product, when exposed to the air in a room, neutralizes cigarette smoke odors, skunk odors, cooking odors, and cat urine odors in carpets. The Gonzo® Odor Eliminator uses volcanic minerals to neutralize odors. OdorFree sells ozone generators that neutralize odors. However, free ozone in a room can be toxic to humans. Rocco & Roxie™ Supply Company produces an enzyme spray product to eliminate stains and odors. In 1996, Proctor & Gamble began marketing a product called Febreze®. This product utilizes cyclodextrin (hydroxyl-propyl-beta-cyclodextrin) as its active ingredient. This chemical does not neutralize odors, but rather inhibits the ability for humans to detect the odors. Some sources state that Febreze® also contains zinc chloride, which neutralizes sulfur odors, such as from onions and rotten eggs. However, zinc chloride is not listed as one of the ingredients of Febreze®. All of these products are just examples of products in this crowded industry.

Noxious odors can be divided into three categories, i.e., acidic odors, basic (or alkaline) odors, and neutral odors. Examples of acidic odors include hydrogen sulfide ($H_2S$) [e.g., hard boiled or rotten eggs] and skunk. Examples of alkaline odors include ammonia, urine, and fish smells. Examples of neutral odors include body odors and putrid odors.

Our U.S. Pat. No. 9,993,573 (referenced above and incorporated herein by reference) discloses a non-toxic, water based, natural, herbal extract odor neutralizing substance that can be sprayed into a room or other confined area, which would neutralize acidic, alkaline, and neutral odors. Although, such a product could include fragrances, the purpose of such a product would be to neutralize the odor rather than to mask the odor.

Our U.S. patent application Ser. No. 15/400,964 (referenced above and incorporated herein by reference) discloses an ultrasonic dispenser that produces a cool, fine aqueous mist. That mist may consist only of water, or it may comprise other substances intended for introduction into the surrounding air. It comprises an electronic cap capable of producing the mist ultrasonically, which sits atop a reservoir filled with liquid. The cap is connected to a programmable device, which in turn is connected to a power source. When the reservoir is filled with the aqueous solution disclosed in our U.S. Pat. No. 9,993,573, the dispenser is able to continuously generate a mist into a closed area that will not mask but will neutralize all types of odors. This aqueous deodorizing chemical solution is but an example of what can be used as an odor neutralizer in this type of device.

However, our dispenser was designed to be small enough to be used by consumers in their homes. Generally, a water-based dispenser effuses a mist for a short duration, usually six to eight hours. Even if the unit were larger with a much larger reservoir, dispensation of the deodorizing mist would take place over a maximum duration of 24 to 28 hours. The reservoir would need to be refilled regularly.

For release into a fixed volume and for a finite time, all dispenser systems do this. However, there is nothing on the market that will allow the emissions to last for a long time period (e.g., one month).

Another problem stems from the fact that a water-based mist is wet. Though it is sprayed into the air, some of it condenses on surfaces leaving a wet film that is somewhat difficult to wipe away.

There is a need for a device that would release a dry fog of deodorizing material into the air of a closed area for a long time. The need extends beyond ordinary consumer applications. It would be desirable for such a deodorizing substance to be able to propagate through air conditioning systems into large areas. It would also be desirable not to require refilling the liquid in the reservoir for a period less than one month.

The problem of the wetness is solved by releasing a vapor (or dry fog) into the air at room temperature rather than a mist. If a droplet particle size is greater than or equal to ten microns ($\geq 10\mu$), it is a mist, and the particles fall like rain. When the particle size is less than or equal to five microns ($\leq 5\mu$), such a vaporous substance is dry. It does not condense. Further, the problem of a short duty cycle is solved by using a large industrial sized reservoir.

Moreover, the smaller the particle size, the greater the deodorizing effect. It is a surface area effect rather than a volume effect. The smaller the particle size, the greater the number of particles, thereby causing the total surface area of the aqueous particles to be higher. The greater the surface area, the more solute can interact chemically with odor causing chemicals. Therefore, the greater the number of particles in the air, the higher the probability of odor neutralization. Thus, with smaller particles, there is a greater effectiveness of deodorization per unit weight of aqueous solution in the air.

SUMMARY OF THE INVENTION

The Present Invention discloses a long-acting ultrasonic dispenser for effusing a water-based deodorizing dry vapor solution into the air of an enclosed volume. The vapor comprises particles containing the solutes dissolved in water, where the particles are each smaller than ten microns. The dispenser comprises a large reservoir connected to a pump that is programmed by a controller to send water into a smaller dispensing chamber. At the bottom of the dispensing chamber is an electrically powered ultrasonic wave generator device comprising a piezoelectric crystal. The ultrasonic device creates waves in the aqueous deodorizing solution that fills the dispensing chamber above the ultrasonic device. One or two electronic sensors connected to the controller dictate when the pump should pour more solution into the chamber. There is a separate chamber within the dispensing chamber into which the electronic sensors are placed so that the level of the water in the dispensing chamber may be measured. Above the surface of the water are generated particles of mist and dry fog. An emitting tube is positioned at the top of the diffusing chamber as also is a fan. At the base of the portion of the emitting tube that is inside the dispensing chamber is a mesh or sieve. The larger mist particles are filtered out and remain in the dispensing chamber. Only the dry fog is emitted from the tube into the air.

The Present Invention also discloses a method for deodorizing obnoxious odors by chemically reacting with odor causing materials for an extended period of time using the disclosed ultrasonic dispenser. A large reservoir is used to contain a water-based solution of deodorizing materials. Using a programmable electronic controller, a quantity of deodorizing solution is pumped into the ultrasonic dispenser as needed. The dispenser then diffuses a dry fog containing the deodorizer into an enclosed area. As the deodorizing solution becomes depleted in the dispenser, more of the solution is pumped into the dispenser as needed. In this way, depending upon the capacity of the large reservoir, the dry fog can be effused into the enclosed area for a desired extended period. This is ideal for incorporation into built-in air conditioning systems in office buildings.

BRIEF DESCRIPTION OF THE DRAWING

There is only one drawing.

FIG. 1 is a schematic drawing of the dispenser of the Present Invention.

DETAILED DESCRIPTION OF THE INVENTION

The Present Invention is an ultrasonic device that dispenses any water-based deodorizing solution continuously for long periods (i.e., for a duration longer than twenty-four hours). The long-acting duration can be for as much as several months.

FIG. 1 is a schematic drawing of the Present Invention. Dispensing chamber 1 comprises electrically powered ultrasonic wave generator 2, an inner chamber 5, an electrically powered fan 10, and an emitting tube 11. Above the ultrasonic generator is the aqueous deodorizer solution, the surface of which is denoted by 3. Examples of aqueous deodorizer solutions that may be used are disclosed in our U.S. Pat. No. 9,993,573. The ultrasonic generator must always be covered by liquid, else the ultrasonic membrane will crack, and the device will quickly become unusable The liquid level necessarily must be above the ultrasonic membrane and preferably between 1 and 4 centimeters above the top surface of the ultrasonic device 2. The crystal must always remain wet. Thus, the level of the aqueous surface 3 must always be controlled. This is done by the electronically powered electronic controller 13, which is a state-of-the-art device. Electrically connected to the controller is at least one electronic liquid level sensor, which is also a state-of-the-art device. Shown in the drawing are two such sensors, i.e., a lower level sensor 6 and an upper level sensor 7. When the liquid level 3 falls below sensor 6, an electrically powered pump 14 will pour water from reservoir 13 into the dispensing chamber 1 via a water input conduit 16 until the level 3 reaches sensor 7. Then it will stop. Thus, the liquid level 3 will always remain at a height in the dispensing chamber between sensor 6 and sensor 7. The reservoir 15 is large enough to hold any desired amount of the aqueous deodorizer liquid solution.

Above the liquid level 3, space or volume 4 contains both aqueous mist (particle size $\geq 10\mu$) and dry fog of aqueous solution (particle size$\approx 5\mu$). At the base of emitter tube 11 is a mesh or sieve 12 with openings small enough that will only permit the dry fog to pass. The fan 10 constantly blows outside air into the dispensing chamber, thus causing the dry for to effuse from emitter tube 11 into the ambient air.

The sensors 6 and 7 must be able to measure the level of liquid surface 3. This is difficult because the ultrasonic action from device 2 causes mist and dry fog to fill volume 4 explosively. Ultrasonic action causes great turbulence in the liquid covering device 2. Thus, the level of liquid surface 3 becomes very difficult to measure. The liquid level is not stable. To solve this problem, we inserted an inner chamber 5 into dispensing chamber 1, into which we placed the electronic liquid level sensors. Toward the bottom of inner chamber 5 are slits 8 and a vent 9, thus allowing liquid to fill the inner chamber 5 from the bottom. The liquid will find its own level (equivalent to that in the main chamber 1. However, there is no liquid turbulence in inner chamber 5. Thus, the liquid level is stable enough to be measured by the sensors.

In the embodiment shown in FIG. 1, two liquid level sensors 6 and 7 are utilized. However, while the two sensors are sufficient to run the dispenser, only one lower level sensor is necessary. In an alternate embodiment of the dispenser in FIG. 1, only lower level sensor 6 is necessary. Upper level sensor 7 can be eliminated. Once sensor 6 detects that the liquid level 3 reaches the lowest allowable point, the controller 13 sends a signal to pump 14 that causes it to send liquid from reservoir 15 through conduit 16 into dispenser chamber 1 for a fixed time calculated to bring liquid surface 3 to a desired level. Thus, the upper liquid level sensor 7 is unnecessary in this embodiment.

Examples of Water-Based Deodorizing Solutions

The following ingredients dissolved in water for exemplary embodiments of the solutions that may be used in the ultrasonic dispenser of the Present Invention. They were initially disclosed in our U.S. Pat. No. 9,993,573.

- *T. indica*
  - *Tamarindus indica*
  - Tamarind
- *R. sativus*
  - Raphanus sativus
  - Radish
- *A. strigosa*
  - Avena Strigosa
  - Lopsided Oat a.k.a. Bristol Oat
- *C. aurantifolia*
  - *Citrus* x *aurantiifolia*
  - Key Lime
- *A. filiculoide*
  - *Azolla filiculoides*
  - Water Fern
- *L. albus*
  - *Lupinus albus*
  - White Lupin a.k.a. Field Lupin
- *O. sanctum*
  - *Ocimum tenuiflorum*
  - Holy Basil a.k.a. tulasi or tulsi
- *C. camphora*
  - *Cinnamomum camphora*
  - Camphor
- Surfactants
- Fragrances
- Buffers
- Preservatives An exemplary embodiment combines following three ingredients taken from the above group must be present in the water-based solution:

1. Tamarind (*T. indica*),
2. Water Fern (*A. filiculoide*), and
3. White Lupin a.k.a. Field Lupin (*L. albus*).

One or more of the other ingredients listed above may be added to the solution to enhance the deodorizing properties of the solution.

The above deodorizing solution is an instance of the type of solution that may be utilized in an exemplary embodiment of the Present Invention. It is not limiting. Any aqueous deodorizing solution may be used, but such solution must be water based.

GLOSSARY

In presenting this disclosure of the Present Invention, the Inventors chose to be their own lexicographers. The definitions of terms shown in this Glossary supersede the plain and ordinary meaning of those terms.

| Term | Meaning |
|---|---|
| Deodorize | A chemical process whereby an odor causing chemical substance is altered or transformed into another substance that no longer produces an odor. |
| Dry Fog | An airborne dry vaporous mass of particles each being an aqueous solution wherein the particle size is less than ten microns, but typically less than or equal to five microns. Dry fog particles generally do not precipitate in air. |
| Fine Mist | An airborne wet collection of liquid droplets each being an aqueous solution wherein the droplet size is greater than or equal to ten microns. |
| Long-Acting | A duration greater than twenty-four hours. Although having twenty-four hours as a lower bound, the duration has no upper bound. |
| Mask/Masking | The overpowering of a malodor with a pleasing odor or a less offensive odor. |
| Mist | An airborne wet collection of liquid droplets each being an aqueous solution. |
| Noxious | A disagreeable or offensive odor; obnoxious odor; a malodor. The substance causing the odor is not necessarily harmful. |
| Ultrasonic Generator | An electronic device comprising a piezoelectric crystal and an ultrasonic membrane capable of vibrating at ultrasonic frequencies and of propagating waves through a liquid. |
| Ultrasonic Membrane | A thin membrane capable of vibrating at ultrasonic frequencies in an ultrasonic generator, wherein when the generator is immersed in liquid, the membrane is positioned between the piezoelectric crystal and the liquid. |
| Water-Based | An aqueous solution. |
| Waer-Based Deodorizing Solution - | Any one of aqueous solution of materials capable of deodorizing noxious odors. |

We claim:

1. A system that dispenses a dry fog comprising a water-based liquid into ambient air in an enclosed volume over a long period, said system comprising:

a) a reservoir that is able to contain the water-based liquid;

b) a dispenser comprising:

i) an enclosed dispensing chamber that is able to contain the water-based liquid, and is separate from the reservoir, wherein the dispensing chamber comprises a top and a bottom;

ii) an electrically powered ultrasonic wave generator positioned at the bottom of the dispensing chamber:

wherein the ultrasonic wave generator comprises a piezoelectric crystal and an ultrasonic membrane each capable of vibrating at ultrasonic frequencies;

iii) an input orifice positioned at the top of the dispensing chamber, wherein the water-based liquid can enter the dispensing chamber;

iv) an inner chamber comprising:
   an inner chamber exterior further comprising a top a bottom, and an enclosure surface;
   at least one slit in the enclosure surface positioned proximate to the bottom of the enclosure surface wherein liquid may enter the inner chamber;
   a vent hole positioned at the top of the inner chamber to allow air to exit the inner chamber;
   at least one liquid level sensor;
v) an electrically powered fan positioned at the top of the dispensing chamber capable of blowing air into the dispensing chamber;
vi) an output orifice positioned at the top of the dispensing chamber, said orifice comprising two ends, wherein one end resides inside the dispensing chamber and the other end resides outside the dispensing chamber;
vii) a mesh, sieve, or filter positioned at the end of the orifice that is inside the dispensing chamber, which is able to pass particles of the water-based liquid sized less than or equal to the maximum size required for the dry fog, and causes droplets of the water-based liquid sized greater than that maximum size to remain inside the dispensing chamber;
c) an electrically powered electronic controller comprising an electrical connection to the at least one liquid level sensor;
d) a water pump electrically connected to the controller and physically connected to the reservoir and the input orifice;
wherein:
   the ultrasonic membrane is always submerged under the water-based liquid;
   the ultrasonic membrane is positioned between the piezoelectric crystal and the water-based liquid;
   the at least one liquid level sensor is positioned to sense a minimum liquid level desired to keep the ultrasonic membrane submerged;
   the at least one liquid level sensor sends a signal to the controller when the liquid level is at the minimum level;
   when the controller receives the signal from the at least one liquid level sensor, the controller causes the pump to engage and to propel the water-based liquid from the reservoir into the dispenser chamber via the input orifice.

2. The system of claim 1 wherein the water-based liquid is a water-based deodorizing solution.

3. The system of claim 2 wherein the dry fog comprises airborne particles of the water-based deodorizing solution.

4. The system of claim 3 wherein the size of the airborne particles of the dry fog is less than ten microns.

5. The system of claim 3 wherein the size of the airborne particles of the dry fog is less than or equal to five microns.

6. The system of claim 4 wherein the mesh, sieve, or filter only permits particles of dry fog sized less than ten microns to pass outside the dispensing chamber via the output orifice.

7. The system of claim 5 wherein the mesh, sieve, or filter only permits particles of dry fog sized less than or equal to five microns to pass outside the dispensing chamber via the output orifice.

8. The system of claim 1 wherein the number of the at least one liquid level sensors is one, and that sensor is positioned in the inner chamber to be able to sense the minimum level.

9. The system of claim 1 wherein the number of the at least one liquid level sensors is two, wherein the first sensor is positioned in the inner chamber to be able to sense the minimum level, and the second sensor is positioned in the inner chamber above the first sensor so as to sense a desired maximum level.

10. The system of claim 1 wherein the output orifice is a fully hollow tube, the cross-section of which is a plane geometric shape.

11. The system of claim 1 wherein the liquid volume capacity of the reservoir is larger than the liquid volume capacity of the dispensing chamber.

12. The system of claim 1 wherein the dry fog is dispensed into the ambient air continuously for a duration longer than twenty-four hours.

13. A method of deodorizing noxious odors in the ambient air using the system of claim 3, said method comprising:
   a) filling the reservoir with a desired volume of the water-based liquid deodorizing solution;
   b) filling the dispensing chamber with the water-based liquid deodorizing solution until it reaches a desired maximum level, wherein said maximum level is greater than a minimum level greater than that required to completely submerge the piezoelectric crystal below the liquid;
   c) sensing the level of the liquid electronically;
   d) activating the ultrasonic wave generator so that an airborne mixture of the water based deodorizing solution comprising both dry fog and mist droplets is generated above the surface of the liquid;
   e) agitating the air above the liquid surface with the fan;
   f) filtering the airborne dry fog and mist droplets through the mesh, sieve, or filter, allowing the dry fog to pass through the output orifice into the ambient air and causing the mist droplets to remain in the dispensing chamber;
   g) reacting the airborne dry fog with materials causing deodorization of the noxious odors;
   h) sending a signal to the controller when the liquid level reaches the minimum level;
   i) pumping a volume of the water-based deodorizing solution from the reservoir into the dispensing chamber via the input orifice;
   j) repeating elements (b) through (i) in sequence indefinitely.

14. The method of claim 13 wherein the dry fog comprises particles of the water-based deodorizing solution having a particle size less than ten microns.

15. The method of claim 14 wherein the particle size is less than or equal to five microns.

16. The method of claim 13 wherein the dry fog chemically reacts with the substances causing the noxious odors so as to eliminate the odors.

17. The method of claim 13 wherein the dry fog is dispensed into the ambient air continuously for a duration longer than twenty-four hours.

* * * * *